United States Patent [19]

Spivack et al.

[11] Patent Number: 4,547,539
[45] Date of Patent: Oct. 15, 1985

[54] SUBSTITUTED (4-HYDROXYPHENYLTHIO) SUCCINIC ANHYDRIDE OR SUCCINATE STABILIZERS

[75] Inventors: John D. Spivack; Stephen D. Pastor, both of Spring Valley, N.Y.

[73] Assignee: Ciba-Geigy Corporation, Ardsley, N.Y.

[21] Appl. No.: 667,190

[22] Filed: Nov. 1, 1984

Related U.S. Application Data

[62] Division of Ser. No. 463,176, Feb. 3, 1983, Pat. No. 4,497,959.

[51] Int. Cl.$^4$ ............................................. C08K 5/36
[52] U.S. Cl. ................................. 524/112; 524/141; 524/289; 524/303
[58] Field of Search ............... 524/112, 289, 303, 141; 528/176, 209, 295; 526/286

[56] References Cited

U.S. PATENT DOCUMENTS

| | | | |
|---|---|---|---|
| 2,952,013 | 4/1976 | Hazard et al. | 424/275 |
| 3,078,290 | 2/1963 | Hechenbleikner et al. | 260/429.7 |
| 3,281,455 | 10/1966 | Steinberg | 524/289 |
| 3,465,029 | 9/1969 | Beirne | 560/15 |
| 3,625,978 | 12/1971 | Geering et al. | 549/253 |
| 3,637,809 | 1/1972 | Kleiner | 524/303 |
| 4,446,264 | 5/1984 | Cottman | 524/289 |

Primary Examiner—Veronica P. Hoke
Attorney, Agent, or Firm—Luther A. Hall

[57] ABSTRACT

Substituted succinic anhydride or succinate stabilizers of the formula I or II

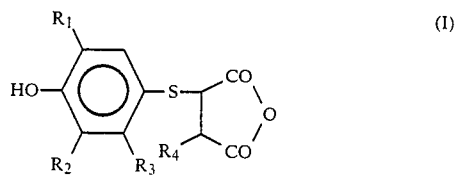

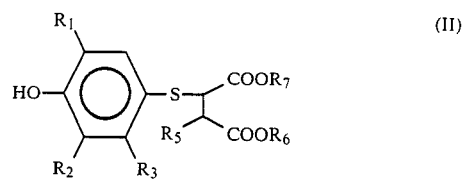

where $R_1$ and $R_2$ are independently alkyl, cycloalkyl, phenyl or aralkyl, $R_3$ is hydrogen or methyl, $R_4$ is hydrogen, lower alkyl or phenyl, $R_5$ is hydrogen, alkyl, alkylthio, arylthio or the structure

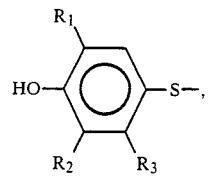

and $R_6$ and $R_7$ are independently hydrogen, alkyl; aryl or substituted aryl are useful as stabilizers for polymeric substrates, particularly polyolefins and rubber.

8 Claims, No Drawings

SUBSTITUTED (4-HYDROXYPHENYLTHIO) SUCCINIC ANHYDRIDE OR SUCCINATE STABILIZERS

This is a divisional of application Ser. No. 463,176 filed on Feb. 3, 1983 now U.S. Pat. No. 4,497,959 issued Feb. 5, 1985.

BACKGROUND OF THE INVENTION

Organic polymeric materials such as plastics and resins, are subject to thermal, oxidative and photo-degradation. A great variety of stabilizers are known in the art for stabilizing a diversity of substrates. Their effectiveness varies depending upon the causes of degradation and the substrate stabilized. In general, it is difficult to predict which stabilizer will be most effective and most economical for any one area of application. For example, stabilizer effectiveness in reducing volatility may depend upon preventing bond scission in the substrate molecule. Limiting embrittlement and retaining elasticity in a polymer or rubber may require prevention of excessive crosslinking and/or chain scission. Prevention of discoloration may require inhibiting reactions which yield new chromophores or color bodies in the substrate or stabilizer. Problems of process stability and incompatibility must also be considered.

It has now been determined that the (hydroxyphenylthio)succinic anhydride or succinate derivatives of this invention possess an unusual combination of desirable properties which makes them particularly effective and useful as stabilizers. The compounds are particularly effective in protecting high impact polystyrene, rubbers such as polybutadiene and styrenebutadiene rubber, and other elastomers wherein retention of elasticity and inhibition of crosslinking, crazing, discoloration, odor formation and exudation are basic requirements.

OBJECTS OF THE INVENTION

It is the primary object of this invention to provide a class of mercaptophenol derivatives which exhibit a broad range of improved stabilization performance characteristics.

Various other objects and advantages of this invention will become evident from the following description thereof.

DETAILED DISCLOSURE

The instant invention pertains particularly to succinic anhydride or succinate derivatives containing one or more groups derived from a hindered mercaptophenol.

These compounds are represented by formula I or II

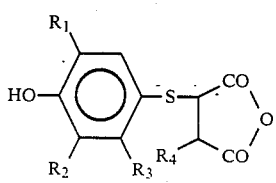
(I)

-continued

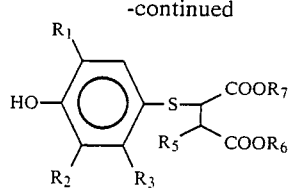
(II)

wherein
$R_1$ and $R_2$ are independently alkyl of 1 to 18 carbon atoms, cycloalkyl of 5 to 6 carbon atoms, phenyl or phenyl substituted by alkyl of 1 to 12 carbon atoms, aralkyl of 7 to 9 carbon atoms or said aralkyl substituted by alkyl of 1 to 12 carbon atoms; $R_2$ may also represent hydrogen;

$R_3$ is hydrogen or methyl;

$R_4$ is hydrogen, alkyl of 1 to 6 carbon atoms or phenyl;

$R_5$ is hydrogen, alkyl of 1 to 6 carbon atoms, alkylthio of 1 to 18 carbon atoms, phenylthio, or a group of the structure

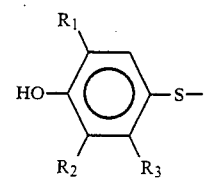

where
$R_1$, $R_2$ and $R_3$ are defined above; and $R_6$ and $R_7$ are independently hydrogen, alkyl of 1 to 30 carbon atoms, alkyl of 2 to 4 carbon atoms substituted by alkenoyloxy of 3 to 4 carbon atoms, phenyl or phenyl substituted by alkyl of 1 to 12 carbon atoms.

$R_1$ and $R_2$ represent straight- or branched-chain alkyl of 1 to 18 carbon atoms such as methyl, ethyl, isopropyl, n-butyl, tert-butyl, tert-amyl, tert-octyl, 2-ethylhexyl, dodecyl or n-octadecyl.

Preferably, when $R_1$ and $R_2$ are alkyl, they represent branched alkyl of 4 to 8 carbon atoms such as tert-butyl, tert-amyl or tert-octyl, and most preferably tert-butyl.

When $R_1$ and $R_2$ are aralkyl, they represent benzyl, alpha-methylbenzyl or alpha, alpha-dimethylbenzyl.

$R_3$ is hydrogen or methyl, preferably hydrogen.

$R_4$ is preferably hydrogen or methyl, and most preferably hydrogen.

$R_5$ is preferably hydrogen, methyl or a group of the structure

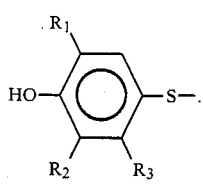

Most preferably $R_5$ is hydrogen.

$R_6$ and $R_7$ may be independently hydrogen, alkyl of 1 to 30 carbon atoms, alkyl of 2 to 4 carbon atoms substituted by alkenoyloxy of 3 to 4 carbon atoms, phenyl or phenyl substituted by alkyl of 1 to 12 carbon atoms.

Preferably $R_6$ and $R_7$ are independently hydrogen, alkyl of 1 to 18 carbon atoms or alkyl of 2 to 4 carbon atoms substituted by alkenoyl of 3 to 4 carbon atoms.

Most preferably $R_6$ and $R_7$ are independently hydrogen, alkyl of 1 to 12 carbon atoms or ethyl substituted by alkenoyloxy of 3 to 4 carbon atoms.

When $R_6$ or $R_7$ is alkyl, they may be for example methyl, ethyl, n-butyl, amyl, 2-ethylhexyl, isooctyl, n-dodecyl, n-octadecyl, eicosyl and tricontyl.

When $R_6$ or $R_7$ is alkyl substituted by alkenoyloxy, they may be ethyl, propyl or butyl, preferably ethyl, substituted by acryloyloxy, methacryloyloxy or crotonyloxy, preferably by acryloyloxy or methacryloyloxy.

The succinic anhydride derivatives of this invention are prepared by reacting the appropriate mercaptophenol with an unsaturated anhydride such as maleic anhydride or citraconic anhydride, optionally in a solvent, in the presence of a proton acceptor. The solvent can be an aromatic hydrocarbon such as benzene, toluene, xylene, and the like, or a heterocyclic ether, such as tetrahydrofuran. The reaction temperature ranges from room temperature to 70° C. The preferred method for preparing the compounds of this invention involves reacting the anhydride with the mercaptophenol in the presence of a proton acceptor such as a tertiary amine, for example, triethylamine or pyridine.

The succinic derivatives can be prepared either by reacting the hydroxyphenylthiosuccinic anhydride, prepared as discussed above, with an appropriate alcohol or substituted alcohol, such as 2-hydroxyethyl acrylate for example, water or phenol to open the anhydride ring; or by reacting the appropriate mercaptophenol, under the same general reaction conditions described for preparing the succinic anhydride derivatives, with a dialkyl or monoalkyl maleate, citraconate or acetylenedicarboxylate.

When a mercaptophenol is added to an acetylenedicarboxylate, two mercaptan groups are added to the molecule and $R_5$ is the group

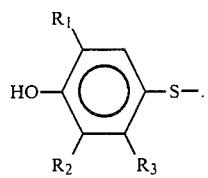

The starting materials for preparing these succinic anhydride and succiate derivatives of the instant invention are items of commerce or can be prepared by known methods.

The preparation of maleate esters is described in Kirk-Othmer, "Encyclopedia of Chemical Technology", 3rd Edit., Vol. 14, John Wiley, New York, 1981, p. 776; and L. K. Flett and W. H. Gardner, "Maleic Anhydride Derivatives", John Wiley, New York, 1952.

The intermediate mercaptophenols correspond to the formula

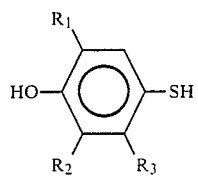

wherein $R_1$, $R_2$ and $R_3$ are as previously defined. Preferred 4-mercaptophenols include 2,6-di-tert.butyl- and 2-tert.-butyl-6-methyl-4-mercaptophenol as well as 2,6-dimethyl-4-mercaptophenol and 2-tert-butyl-5-methyl-4-mercaptophenol.

The compounds of this invention are effective in stabilizing organic materials such as plastics, polymers and resins.

The compounds of the invention are particularly useful as stabilizers, especially for the protection of polyolefins, both homopolymers or copolymers, for instance, polyethylene, polypropylene, polyisobutylene, poly(butene-1), poly(pentene-1), poly(3-methylbutene-1), poly(4-methyl-pentene-1), various ethylene-propylene copolymers, EPM, EPDM and the like, polystyrene, and its copolymers or terpolymers, including impact polystyrene, ABS resins, SBR, polyisoprene, polybutadiene, nitrile rubber, as well as natural rubber, polyesters including polyethylene terephthalate and polybutylene terephthalate, including copolymers.

Polyurethanes, polycarbonates, polyamides such as nylon 6, 6/6 and the like as well as copolyamides and polysulfones are also stabilized.

In general, polymers which can be stabilized include:

1. Polymers of monoolefins and diolefins, for example polyethylene α which optionally can be crosslinked), polypropylene, polyisobutylene, polybutene-1, poly-methylpentene-1, polyisoprene or polybutadiene, as well as polymers of cycloolefins, for instance of cyclopentene or norbornene.

2. Mixtures of the polymers mentioned under (1), for example mixtures of polypropylene with polyethylene or with polyisobutylene.

3. Copolymer of monoolefins and diolefins with each other or with other vinyl monomers, such as, for example, ethylene/propylene, propylene/butene-1, propylene/isobutylene, ethylene/butene-1, propylene/-butadiene, isobutylene/isoprene, ethylene/ethyl acrylate, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene norbornene.

4. Polystyrene.

5. Random copolymers of styrene of α-methylstyrene with dienes or acrylic derivatives, such as, for example, styrene/butadiene, styrene/acrylonitrile, styrene/alkyl methacrylates, styrene/acrylonitrile/methyl acrylate; mixtures of high impact strength from styrene copolymers and another polymer, such as, for example, from a polyacrylate, a diene polymer or an ethylene/-propylene/diene terpolymer; and block copolymers of styrene, such as, for example, styrene/butadiene/styrene, styrene/isoprene/styrene, styrene/ethylene/-butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5, for instance the copolymer mixtures known as ABS-, MBS-, ASA- or AES-polymers.

7. Halogen-containing polymers, such as polychloroprene, chlorinated rubbers, chlorinated or sulfochlorinated polyethylene, polymers from halogen-containing vinyl compounds, as for example, polyvinyl chloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamides and polyacrylonitrile.

9. Copolymers from the monomers mentioned under (8) with each other or with other unsaturated monomers, such as, for instance, acrylonitrile/butadiene, acrylonitrile/alkyl acrylate or acrylonitrile/vinyl chloride copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallylmelamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as a comonomer.

13. Polyphenylene oxides and sulfides.

14. Polyurethanes which are derived from polyethers, polyesters or polybutadienes with terminal hydroxyl groups on the one side and aliphatic or aromatic polyisocyanates on the other side, as well as precursors thereof.

15. Polyamides and copolyamides which are derived from diamines and dicarboxylic acids and/or from aminocarboxylic acids of the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene isophthalamide, as well as copolymers thereof with polyethers, such as for instance, with polyethylene glycol, polypropylene glycol or polytetramethylene glycols.

16. Polyureas, polyimides and polyamide-imides.

17. Polyesters which are derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate and polyhydroxybenzoates as well as block copolyether-esters derived from polyethers having hydroxyl end groups.

18. Polycarbonates.

19. Polysulfones and polyethersulfones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides and aromatic diepoxides.

26. Natural polymers, such as cellulose, rubber, gelatin and derivatives thereof which are chemically modified in a polymer-homologous manner, such as cellulose acetates, cellulose propionates and cellulose butyrates, or the cellulose ethers, such as methylcellulose.

27. Naturally occurring and synthetic organic materials which are pure monomeric compounds or mixtures of such compounds, for example mineral and mineral lubricating oils, animal and vegetable fats, oils and waxes, or oils, fats and waxes based on synthetic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.

28. Aqueous emulsions of natural or synthetic rubber, e.g. natural latex or latices of carboxylated styrene/butadiene copolymers.

In general, the stabilizers of this invention are employed in from about 0.01 to about 5% by weight of the stabilized composition, although this will vary with the particular substrate and application. An advantageous range is from about 0.05 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain various conventional additives, such as the following:

1. Antioxidants:

1.1. Simple 2.6-dialkylphenols, such as, for example, 2,6-di-tert.-butyl-4-methylphenol, 2-tert.-butyl-4,6-dimethylphenol, 2,6-di-tert.-butyl-4-methoxymethylphenol and 2,6-di-octadecyl-4-methylphenol.

1.2. Derivatives of alkylated hydroquinones, such as, for example, 2,5-di-tert.-butyl-hydroquinone, 2,5-di-tert.-amylhydroquinone, 2,6-di-tert.-butyl-hydroquinone, 2,6-di-tert.-butyl-4-hydroxy-anisole, 3,5-di-tert.-butyl-4-hydroxy-anisole, tris-(3,5-di-tert.-butyl-4-hydroxyphenyl)phosphite, 3,5-di-tert.-butyl-4-hydroxyphenyl stearate and bis-(3,5-di-tert.-butyl-4-hydroxyphenyl)adipate.

1.3. Hydroxylated thiodiphenyl ethers, such as, for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxy-phenyl)disulphide.

1.4. Alkylidene-bisphenols, such as, for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol), 4,4'-methylene-bis-(2,6-di-tert.-butyl-phenol), 2,6-di-(3-tert.-butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxphenyl)-butane, 1,1-bis-(5- tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercaptobutane, 1,1,5,5-tetra-(5-tert.-butyl-4-hydroxy-2-methylphenyl)-pentane and ethylene glycol bis-[3,3-bis-(3′-tert.-butyl-4′-hydroxyphenyl)-butyrate].

1.5. O-, N- and S-benzyl compounds, such as, for example, 3,3′;5,5′-tetra-tert.-butyl-4,4′-dihydroxydibenzyl ether, octadecyl 4-hydroxy-3,5-dimethylbenzylmercaptoacetate, tris-(3,5-di-tert.-butyl-4-hydroxybenzyl)-amine and bis-(4-tert.-butyl-3-hydroxy-2,6-dimethylbenzyl)dithioterephthalate.

1.6. Hydroxybenzylated malonates, such as, for example, dioctadecyl 2,2-bis-(3,5-di-tert.-butyl-2-hydroxybenzyl)-malonate, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-[4-(1,1,3,3-tetramethylbutyl)-phenyl] 2,2-bis-(3,5-di-tert.-butyl-4-hydroxybenzyl)-malonate.

1.7. Hydroxybenzyl-aromatic compounds, such as, for example, 1,3,5-tris-(3,5-di-tert.-butyl-4-hydroxybenzyl)-2,4,6-trimethylbenzene, 1,4-bis-(3,5-di-tert.-butyl-4-hydroxybenzyl)-2,3,5,6-tetramethylbenzene and 2,4,6-tri-(3,5-di-tert.-butyl-4-hydroxybenzyl)-phenol.

1.8. s-Triazine compounds, such as, for example, 2,4-bis-octylmercapto-6-(3,5-di-tert.-butyl-4-hydroxyanilino)-s-triazine, 2-octylmercapto-4,6-bis-(3,5-di-tert.-butyl-4-hydroxyanilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert.-butyl-4-hydroxyphenylethyl)-s-triazine and 1,3,5-tris-(3,5-di-tert.-butyl-4-hydroxybenzyl)isocyanurate.

9. Amides of β-(3,5-di-tert.-butyl-4-hydroxyphenyl)-propionic acid, such as, for example, 1,3,5-tris-3,5-di-tert.-butyl-4-hydroxyphenyl-propionyl)-hexahydro-s-triazine and N,N′-di-(3,5-di-tert.-butyl-4-hydroxyphenyl-propionyl)-hexamethylenediamine. N,N′-bis-β-(3,5-di-t-butyl-4-hydroxyphenylpropionyl)-hydrazine.

1.10. Esters of β-(3,5-di-tert.-butyl-4-hydroxyphenyl)propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, triethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo-[2,2,2]octane.

1.11. Esters of β(5-tert.-butyl-4-hydroxy-3-methylphenyl)propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, triethylene glycol, thiodiethylene glycol, neopentylglycol, pentaerythritol, 3-thia-undecanol, 3-thia-pentadecanol, trimethylhexanediol trimethyolethane, trimethylolpropane, tris-hydroxyethyl isocyanurate and 4-hydroxymethyl-1-phospha-2,6,7-trioxabicyclo[2,2,2]octane.

1.12. Esters of 3,5-di-tert.-butyl-4-hydroxyphenylacetic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiglycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2,2,2]-octane, especially the tetra-bis ester of pentaerythritol.

1.13. Benzylphosphonates, such as, for example, dimethyl 3,5-di-tert.-butyl-4-hydroxybenzyl-phosphonate, diethyl 3,5-di-tert.butyl-4-hydroxybenzyl-phosphonate, dioctadecyl 3,5-di-tert.butyl-4-hydroxybenzyl-phosphonate and dioctadecyl 5-tert.-butyl-4-hydroxy-3-methylbenzyl-phosphonate.

The following may be mentioned as examples of further additives that can be used together with the stabilizer of this invention and the antioxidant:

1. Aminoaryl derivatives, e.g. phenyl-1-naphthylamine, phenyl-2-naphthylamine, N,N′-diphenyl-p-phenylenediamine, N,N′-di-2-naphthyl-p-phenylenediamine, N,N′-di-naphthyl-p-phenylenediamine, N,N′-di-sec.-butyl-p-phenylenediamine, 6-ethoxy-2,2,4-trimethyl-1,2-dihydroquinoline, 6-dodecyl-2,2,4-trimethyl-1,2-dihydroquinoline, mono- and dioctyliminodibenzyl, polymerized 2,2,4-trimethyl-1,2-dihydroquinoline.

Octylated diphenylamine, nonylated diphenylamine, N-phenyl-N′-cyclohexyl-p-phenylenediamine, N-phenyl-N′-isopropyl-p-phenylenediamine, N,N′-di-sec.octyl-p-phenylenediamine, N-phenyl-N′-sec.-octyl-p-phenylenediamine, N,N′-di-(1,4-dimethylpentyl)-p-phenylenediamine, N,N′-dimethyl-N,N′-di-(sec.-octyl)-p-phenylenediamine, 2,6-dimethyl-4-methoxyaniline, 4-ethoxy-N-sec.-butylaniline, diphenylamineacetone condensation product, aldol-1-naphthylamine and phenothiazine.

Discoloration effects have to be taken into account when using the above antioxidants.

2. UV-Absorbers and light-stabilising agents 2.1. 2-(2′-Hydroxyphenyl)-benzotriazoles, e.g. the 5′-methyl-, 3′,5′-di-tert.-butyl-, 5′-tert.butyl-, 5′-(1,1,3,3-tetramethylbutyl)-, 5-chloro-3′,5′-di-tert.-butyl-, 5-chloro-3′-tert.-butyl-5′-methyl-, 3′-sec.-butyl-5′-tert.-butyl-, 3′-alpha-methylbenzyl-5′-methyl-, 3′-alpha-methylbenzyl-5′-methyl-5-chloro-, 4′-hydroxy-, 4′-methoxy-, 4′-octoxy-, 3′,5′-di-tert.-amyl-, 3′-methyl-5′-carbomethoxyethyl-, 3′,5′-bis(alpha,alpha-dimethylbenzyl),3′,5′-bis(alpha,alpha-dimethyl benzyl)-5-chloro-, 3′,5′-di-tert.-octylphenyl, 3′,5′-di-tert.-octylphenyl-5-chloro- and 5-chloro-3′,5′-di-tert.-amyl-derivatives.

2.2. 2,4-bis-(2′-Hydroxyphenyl)-6-alkyl-s-triazines, e.g. the 6-ethyl-, 6-heptadecyl- or 6-undecyl-derivative.

2.3. 2-Hydroxybenzophenones, e.g. the 4-hydroxy-, 4-methoxy-, 4-octoxy-, 4-decyloxy-, 4-dodecyloxy-, 4-benzyloxy-, 2′,44′-trihydroxy- or 2′-hydroxy-4,4′-dimethoxy-derivative.

2.4. 1,3-bis-(2′-Hydroxybenzoyl)-benzenes, e.g. 1,3-bis-(2′-hydroxy-4′-hexyloxy-benzoyl)-benzene, 1,3-bis-(2′-hydroxy-4′-octyloxy-benzoyl)-benzene or 1,3-bis-(2′-hydroxy-4′dodecyloxy-benzoyl)-benzene.

2.5. Esters of optionally substituted benzoic acids, e.g. phenylsalicylate, octylphenylsalicylate, dibenzoylresorcin, bis-(4-tert.-butylbenzoyl)-resorcin, benzoylresorcin, 3,5-di-tert.-butyl-4-hydroxybenzoic acid-2,4-di-tert.-butylphenyl ester or -octadecyl ester or n-hexadecyl ester or -2-methyl-4,-6-di-tert.-butyl ester.

2.6. Acrylates, e.g. α-cyano-β,β-diphenylacrylic acid-ethyl ester or -isooctyl ester, α-carbomethoxy-cinnamic acid methyl ester, α-cyano-β-methyl-p-methoxy-cinnamic acid methyl ester or butyl ester or N-(β-carbomethoxyvinyl)-2-methyl-indoline.

2.7. Sterically hindered amines, e.g. 4-benzoyl-2,2,6,6-tetramethylpiperidine, 4-stearyl-oxy-2,2,6,6-tetramethylpiperidine, bis-(2,2,6,6-tetramethylpiperidyl)-sebacate or 3-n-octyl-7,7,9,9-tetramethyl-1,3,8-triazaspiro[4,5]decane-2,4-dione. 2.8. Oxalic acid diamides, e.g. 4,4'-di-octyloxy-oxanilide, 2,2'-di-dodecyloxy-5,5'-di-tert.-butyl-oxanilide, 2-ethoxy-2'-ethyl-oxanilide, N,N'-bis-(3-dimethyl-aminopropyl)-oxalamide, 2-ethoxy-5-tert.-butyl-2'-ethyl-5,4'-di-tert.-butyl-oxanilide, or mixtures of ortho- and para-methoxy- as well as of o- and p-ethoxy-disubstituted oxanilides.

3. Metal deactivators, e.g. oxanilide, isophthalic acid dihydrazide, sebacic acid-bis-phenylhydrazide, bis-benzylidene-oxalic acid dihydrazide, N,N'-diacetyl-adipic acid dihydrazide, N,N'-bis-salicyloyloxalic acid dihydrazide, N,N'-bis-salicyloylhydrazine, N,N'-bis-(3,5-di-tert.-butyl-4-hydroxyphenylpropionyl)-hydrazine, N-salicyloyl-N'-salicylalhydrazine, 3-salicyloyl-amino-1,2,4-triazole or N,N'-bis-salicyloyl-thiopropionic acid dihydrazide.

4. Basic co-stabilisers, e.g. alkali metal salts and alkaline-earth metal salts of higher fatty acids, for example Ca-stearate, Zn-stearate, Mg-behenate, Na-ricinoleate or K-plamitate.

5. Nucleation agents, e.g. 4-tert.-butylbenzoic acid, adipic acid or diphenylacetic acid.

6. Phosphites, such as, for example, triphenyl phosphite, diphenylalkyl phosphites, phenyldialkyl phosphites, tri-(nonylphenyl)phosphite, trilauryl phosphite, trioctadecyl phosphite, 3,9-di-n-octadecyloxy- or 3,9-bis(2,4-di-tert-butylphenyloxy)-2,4,8,10-tetraoxa-3,9-diphosphaspiro[5.5]undecane, and tri-(4-hydroxy-3,5-di-tert.butylphenyl)phosphite.

Other additives that can be incorporated in the stabilized compositions are thiosynergists such as dilaurylthiodipropionate or distearylthiodipropionate, lubricants such as stearyl alcohol fillers, carbon black, asbestos, kaolin, talc, glass fibers, pigments, optical brighteners, flameproofing agents and antistatic agents.

The compounds of this invention may be used alone as the sole stabilizer having either mainly an antioxidant function or a light stabilizing function or the stabilizer may combine utility as an antioxidant and light stabilizer. The stabilizers may be used with phenolic antioxidants, lubricants such as calcium stearate, pigments, colorants or dyes, UV absorbers, light stabilizers such as hindered amines, metal deactivators, talc and other fillers, etc.

The compounds of this invention are particularly useful in stabilizing organic materials when combined with a dialkyl thiodipropionate such as distearyl thiodipropionate or dilauryl thiodipropionate. This is true especially for polyolefins and for polypropylene in particular.

The instant compounds also are especially effective in combination with organic phosphites in the stabilization of organic materials. Polyolefins, such as polyethylene and particularly polypropylene, as well as polystyrene and various hydrocarbon elastomers are well stabilized by this combination of stabilizers.

Organic phosphites found to be especially useful include tri(nonylphenyl)phosphite, trilauryl phosphite, tris(3,5-ditert-butyl-4-hydroxyphenyl)phosphite, 3,9-di-n-octadecyloxy-2,4,8,10-tetraoxa-3,9-diphosphaspiro[5.5]undecane, 3,9-bis(2,4-di-tert-butylphenyloxy)-2,4,8,10-tetraoxa-3,9-diphosphaspiro[5.5]undecane and tris[2-(2,4,8,10-tetra-tert-butyl-dibenzo[d,f]-1,3,2-dioxaphosphipan-6-yloxy)ethyl]amine or mixtures thereof.

The following examples are presented for the purpose of illustration only and are not to be construed to limit the nature or scope of the instant invention in any manner whatsoever.

EXAMPLE 1

Dimethyl 2,3-bis(3,5-di-tert-butyl-4-hydroxyphenylthio)succinate

In a 300 ml flame-dried flask under nitrogen, a solution of 23.84 grams of 3,5-di-tert-butyl-4-mercaptophenol and 0.5 grams triethylamine in 100 ml toluene is slowly treated with a solution of 7.11 grams of dimethyl acetylenedicarboxylate in 50 ml toluene, maintaining the temperature below 30° C. The reaction mixture is stirred overnight, the solvent then removed in vacuo, and the residue recrystallized from a 1:1 heptane:toluene mixture to give 22.06 grams (71% yield) of while solid. Proton NMR is consistent with a threo-meso isomer mixture.

Anal. Calcd. for $C_{34}H_{50}O_6S$: C, 66.0; H, 8.1. Found: C, 66.3; H, 8.0.

EXAMPLE 2

Dimethyl 2-(3,5-di-tert-butyl-4-hydroxyphenylthio)succinate

The procedure of Example 1 is repeated using 23.84 grams of 2,6-di-tert-butyl-4-mercaptophenol, 14.41 grams of dimethyl maleate, and 0.5 grams of triethylamine. The product is recrystallized from heptane to give 30.44 grams (80% yield) of white solid, m.p. 94°–96° C.

Anal. Calcd. for $C_{20}H_{30}O_5S$: C, 62.8; H, 7.9. Found: C, 63.0; H, 8.0.

EXAMPLE 3

Di-n-butyl 2-(3,5-di-tert-butyl-4-hydroxyphenylthio)succinate

The procedure of Example 1 is repeated using 11.92 grams of 2,6-di-tert-butyl-4-mercaptophenol, 11.41 grams of di-n-butyl maleate, and 0.5 gram of triethylamine. The product is purified by dry column chromatography to give a clear syrup.

Anal. Calcd. for $C_{26}H_{42}O_5S$: C, 66.9; H. 9.1. Found: C, 66.8; H, 8.7.

EXAMPLE 4

Di-n-dodecyl 2-(3,5-di-tert-butyl-4-hydroxyphenylthio)succinate

The procedure of Example 1 is repeated using 7.15 grams of 2,6-di-tert-butyl-4-mercaptophenol, 13.58 grams of di-n-dodecyl maleate, and 0.3 gram of triethylamine. The product is purified by dry column chromatography to give a clear liquid.

Anal. Calcd. for $C_{42}H_{74}O_5S$: C, 73.0; H, 10.8. Found: C, 73.0; H, 10.8.

EXAMPLE 5

2-(3,5-Di-tert-butyl-4-hydroxyphenylthio)succinic anhydride

The procedure of Example 1 is repeated using 23.84 grams of 2,6-di-tert-butyl-4-mercaptophenol, 9.8 grams of maleic anhydride, and 0.51 grams of triethylamine. The residue is recrystallized once from hexane-toluene mixture and once from cyclohexane to give 19.0 grams of a light yellow solid, m.p. 92°–93° C.

Anal. Calcd. for $C_{18}H_{24}O_4S$: C, 64.3; H, 7.2. Found: C, 64.2; H, 7.5.

EXAMPLE 6

2-(3,5-Di-tert-butyl-4-hydroxyphenylthio)succinic acid, 2-acryloyloxyethyl monoester In a flame-dried flask under nitrogen, a mixture of 8.41 grams of 2-(3,5-di-tert-butyl-4-hydroxyphenylthio)succinic anhydride and 2.90 grams of 2-hydroxyethyl acrylate is heated at 70°–80° C. for one hour. The residue is recrystallized from a toluene: petroleum ether mixture twice to give 3.86 grams of an off-white solid, m.p. 89°–91° C.

Anal. Calcd. for $C_{23}H_{32}O_7S$: S, 7.1. Found: S, 7.0.

EXAMPLE 7

This example illustrates the stabilizing effectiveness of the instant stabilizer combination in impact polystyrene (IPS).

A solution of eight weight percent polybutadiene rubber (Firestone DIENE 55) dissolved in styrene monomer is prepared on a roller mill. The indicated amount of stabilizer is also introduced at this point. 500 ppm of zinc stearate is added to aid in removing the sample from the bottle after the polymerization. The bottle is screwed into the polymerization apparatus which is equipped with a double helical ribbon stirrer. Since most commercial IPS bulk polymerizations are thermally initiated processes, no initiator is used in the laboratory process. A nitrogen atmosphere is established and then the reactor is heated to 121° C. within ½ hour. Heating is continued at 121° C. with efficient stirring until there is a 30 to 35% monomer conversion (ca. 2½ hours). The stirring rate is controlled to yield a two to four micron rubber particle size. The bottles are removed from the polymerization apparatus, blanketed with nitrogen, capped, and then placed in a fluidized bed sand bath to complete the polymerization. The bottles are heated in the bath in the following fashion: one hour at 100° C. to equilibrate the temperature, one hour to reach 140° C. and then an additional eight hours with the temperature increasing at the rate of 10° C. per hour to a maximum of 220° C. After the resin cools, the bottle is broken and the glass removed. The average weight of the polymer block obtained is slightly over 600 grams. The block is then placed in a vacuum oven at 200° C. and a vacuum of 1 mm Hg applied as the polymer is heated for 45 minutes in order to remove all volatiles. The block is then removed from the oven, immediately placed in a heated (205° C.) hydraulic press and then pressed into a thick slab between two sheets of aluminum foil (three minutes heating, five minutes in a cold press). The slab is split with a band saw and the pieces are granulated. All batches are extruded at 205° C. and then pelletized. The pellets are compression molded at 205° C. into 125 mil (3.175 mm) tensile bars. The bars are then aged at 150° C. on glass plates placed on rotating shelves in a forced air oven. Other tensile bars are aged at 80° C. suspended from rotating shelves in a forced air oven. The specimen yellowness index is determined on the bars at various intervals according to ASTM D-1925-63T. Correspondingly, the bars are periodically measured for percent elongation in the Instron Tensile Testing Apparatus (Instron Engineering Corporation, Massachusetts) at a pull rate of 5 mm/minute according to ASTM D638. The results of these tests are given below.

| | | Oven Aged Samples @ 80° C. | | | | |
|---|---|---|---|---|---|---|
| | % by weight | Hours at 80° C. | | | | |
| % Elongation | Conc. Add. | 0 | 300 | 600 | 900 | 1200 |
| Additive | | | | | | |
| None | — | 33 | 9 | 3 | 3 | 3 |
| Compound of Example 5 | 0.1 | 50 | 49 | 28 | 12 | 7 |
| Yellowness Index | | | | | | |
| None | — | 7 | 14 | 45 | 59 | —* |
| Compound of Example 5 | 0.1 | −3 | 0 | 0 | 2 | 7 |

| | | Oven Aged Samples @ 150° C. | | | |
|---|---|---|---|---|---|
| | % by weight | Hours at 150° C. | | | |
| % Elongation | Conc. Add. | 0 | ½ | 1 | 1½ |
| Additive | | | | | |
| None | — | 33 | 7 | 7 | 3 |
| Compound of Example 5 | 0.1 | 50 | 23 | 13 | 3 |
| Yellowness Index | | | | | |
| None | — | 7 | 18 | 30 | 38 |
| Compound of Example 5 | 0.1 | −3 | 1 | 12 | 22 |

EXAMPLE 8

Light Stability of Polypropylene

Unstabilized polypropylene powder (Hercules Profax 6501) is thoroughly blended with the indicated amount (% by weight) of additive. The blended materials are then milled on a two roll mill at 182° C. for 5 minutes, after which time the stabilized polypropylene is sheeted from the mill and allowed to cool. The milled polypropylene is then cut into pieces and compression molded on a hydraulic press at 220° C. and 175 psi ($1.2 \times 10^6$ Pa) into 5 mil (0.127 mm) films. The sample is exposed in a fluorescent sunlight/black light (FS/BL) chamber. Failure is taken as the hours required to reach 0.5 carbonyl absorbance by infrared spectroscopy on the exposed films.

| Additive | Additive Conc. (% by weight) | FS/BL Test Results (Hours to Failure) |
|---|---|---|
| None | — | 200–300 |
| Compound of Example 2 | 0.2 | 360 |
| Compound of Example 3 | 0.2 | 400 |
| Compound of Example 5 | 0.2 | 420 |

What is claimed is:

1. A composition of matter comprising an organic material subject to oxidative, thermal or actinic-induced degradation selected from the group consisting of naturally occurring and synthetic polymers, resins, oils, fats and waxes stabilized with an effective stabilizing amount of a compound having formula I or II

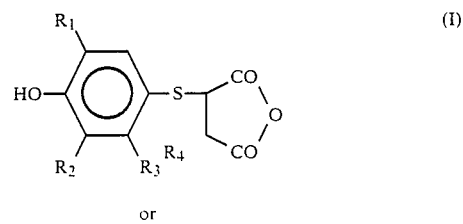

or

-continued

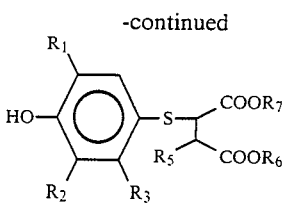
(II)

wherein
R$_1$ and R$_2$ are independently alkyl of 1 to 18 carbon atoms, cycloalkyl of 5 to 6 carbon atoms, phenyl or phenyl substituted by alkyl of 1 to 12 carbon atoms, aralkyl of 7 to 9 carbon atoms or said aralkyl substituted by alkyl of 1 to 12 carbon atoms; R$_2$ may also represent hydrogen;
R$_3$ is hydrogen or methyl;
R$_4$ is hydrogen, alkyl of 1 to 6 carbon atoms or phenyl;
R$_5$ is hydrogen, alkyl of 1 to 6 carbon atoms, alkylthio of 1 to 18 carbon atoms, phenylthio, or group of the structure

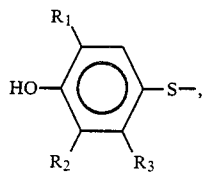

where R$_1$, R$_2$ and R$_3$ are defined above; and
R$_6$ and R$_7$ are independently hydrogen, alkyl of 1 to 30 carbon atoms, alkyl of 2 to 4 carbon atoms substituted by alkenoyloxy of 3 to 4 carbon atoms, phenyl or phenyl substituted by alkyl of 1 to 12 carbon atoms.

2. A composition according to claim 1 wherein the organic material is a synthetic polymer.

3. A composition according to claim 2 wherein the polymer is a polyolefin homopolymer or copolymer.

4. A composition according to claim 2 wherein the polymer is a styrene homopolymer, copolymer or terpolymer.

5. A composition according to claim 1 which also contains an effective stabilizing amount of a coadditive which is a dialkyl thiodipropionate.

6. A composition according to claim 1 which also contains an effective stabilizing amount of an organic phosphite.

7. A composition according to claim 6 wherein the organic phosphite is tri(nonylphenyl)phosphite, trilauryl phosphite, tris(3,5-di-tert-butyl-4-hydroxyphenyl)phosphite, 3,9-di-n-octadecyloxy-2,4,8,10-tetraoxa-3,9-diphosphaspiro[5.5]undecane, 3,9-bis(2,4-di-tert-butylphenyloxy)-2,4,8,10-tetraoxa-3,9-diphosphaspiro[5.5]undecane or tris[2-(2,4,8,10-tetratert-butyl-dibenzo[d,f]-1,3,2-dioxaphosphepin-6-yloxy)ethyl]amine or mixtures thereof.

8. A method of stabilizing an organic material against oxidative, thermal or actinic-induced degradation selected from the group consisting of naturally occurring and synthetic polymers, resins, oils, fats and waxes which comprises incorporating into said organic material an effective stabilizing amount of a compound having formula I or II

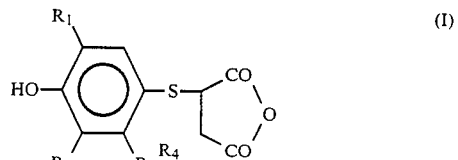
(I)

or

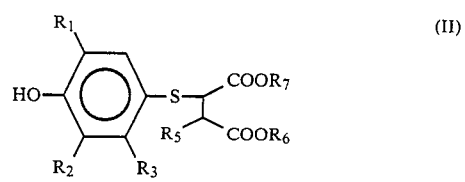
(II)

wherein
R$_1$ and R$_2$ are independently alkyl of 1 to 18 carbon atoms, cycloalkyl of 5 to 6 carbon atoms, phenyl or phenyl substituted by alkyl of 1 to 12 carbon atoms, aralkyl of 7 to 9 carbon atoms or said aralkyl substituted by alkyl of 1 to 12 carbon atoms; R$_2$ may also represent hydrogen;
R$_3$ is hydrogen or methyl;
R$_4$ is hydrogen, alkyl of 1 to 6 carbon atoms or phenyl;
R$_5$ is hydrogen, alkyl of 1 to 6 carbon atoms, alkylthio of 1 to 18 carbon atoms, phenylthio, or group of the structure

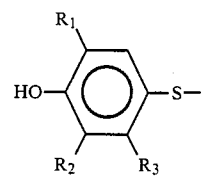

where R$_1$, R$_2$ and R$_3$ are defined above; and
R$_6$ and R$_7$ are independently hydrogen, alkyl of 1 to 30 carbon atoms, alkyl of 2 to 4 carbon atoms substituted by alkenoyloxy of 3 to 4 carbon atoms, phenyl or phenyl substituted by alkyl of 1 to 12 carbon atoms.

* * * * *